Feb. 25, 1969 W. ZOMBORY ET AL Plant Pat. 2,867
DIANTHUS PLANT
Filed Aug. 17, 1967
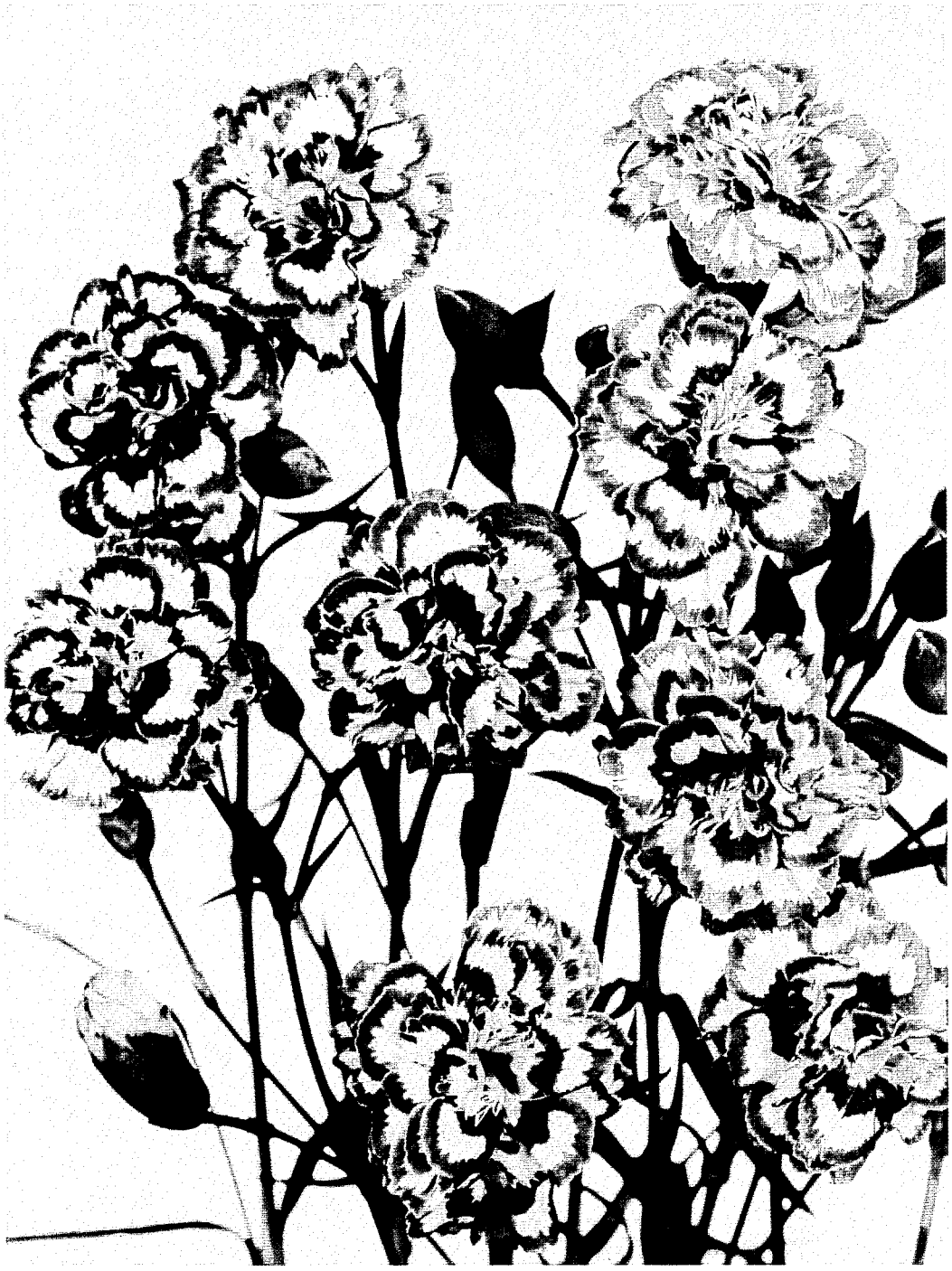
Inventors.
William Zombory
Sophia B. Zombory
By: Robb & Robb
Attorneys.

United States Patent Office

Plant Pat. 2,867
Patented Feb. 25, 1969

2,867
DIANTHUS PLANT

William Zombory and Sophia B. Zombory, Detroit, Mich., assignors to Jackson & Perkins Company, Newark, N.Y., a corporation of New York Filed Aug. 17, 1967, Ser. No. 661,482
U.S. Cl. Plt.—70 1 Claim
Int. Cl. A01h 5/02

The present invention relates to a new and distinct variety of dianthus plant which was originated by us by crossing an unnamed and unpatented dianthus seedling derived from a cross of the dianthus variety known as "Pink Butterfly" (unpatented) × an unnamed and unpatented white-flowered dianthus seedling of the species botanically known as *"Dianthus allwoodi,"* with another unnamed and unpatented dianthus seedling derived from an unnamed and unpatented show-pink *allwoodi* seedling × an unnamed and unpatented laced pink *allwoodi* seedling.

The primary objective of this breeding was to produce a new dianthus variety having the everblooming habit and compact form of *Dianthus allwoodi,* but which bears flowers of a different color. This objective was fully achieved, along with other desirable improvements, as evidenced by the following unique combination of characteristics which are outstanding in the new variety and which distinguish it from its parents, as well as from all other varieties of which we are aware:

(1) A compact habit of plant growth;

(2) An everblooming habit;

(3) Attractive foliage of Andover Green color, with a silvery sheen of Artemisia Green;

(4) Good flower petalage ranging from 20 to 25 petals per flower; and (5) A distinctive and attractive general color tonality of the flowers corresponding to Pale Cinnamon Pink, with the petals edged with Carmine and the lower half of the petals being overcast with Bordeaux.

Asexual reproduction of our new dianthus variety by cuttings, as performed at Detroit, Mich., and also at Newark, N.Y., shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with Ridgway's Color Standards and Nomenclature:

Parentage: Seedling.

*Seed parent.*—An unnamed seedling derived from a cross of "Pink Butterfly" × an unnamed white-flowered *allwoodi* seedling.

*Pollen parent.*—An unnamed seedling derived from a cross of an unnamed show-pink *allwoodi* seedling × an unnamed laced pink *allwoodi* seedling.

Blooming season: Starts blooming the first year from cuttings, beginning in June and continuing during July and again during September.

*Plant*

Growth: About 12 inches tall; compact.

Leaves: Many bottom leaves in tufts; from about 2½ inches to 3 inches long; narrow; thick. Color—Andover Green, Plate 47, with a silvery sheen of Artemisia Green, Plate 47.

Flower stem: About 12 inches long; strong; stiff; bears from 3 to 5 flowers per stem. Color—Slate, Olive, Plate 47.

*Flower*

Borne: Mostly on own-branched stalks; some on the laterals nearly sessile.

Size: About 2 inches in diameter.

Petals: From 20 to 25 per flower; nearly entire. Color: upper side—Pale Cinnamon Pink, Plate 29, with petals edged with Carmine, Plate 1, and with lower half of petals overcast with Bordeaux, Plate 12; reverse side—White, Plate 53, faintly overcast with Rosolane Pink, Plate 26 on the outer edge of the petals.

Claw: White, Plate 53, blended with Light Turtle Green, Plate 32.

Calyx: Cylindrical and splits in the open stages of the flower.

*Color.*—Light Hellebore Green, Plate 17.

*Teeth.*—About ½ inch long; erect. Color—Light Bice Green, Plate 17.

Bracts: 3 in number; medium size. Color—Yew Green, Plate 31.

Stamens: About 10 in number. Color—White, Plate 53.

Anthers: Color—Pale Lilac, Plate 37.

Ovary: Small; ovoid.

Fragrance: Sweet. Nature—old spice.

We claim:

1. A new and distinct variety of dianthus plant, substantially as herein shown and described, characterized particularly as to novelty by the unique combination of a compact habit of plant growth, an everblooming habit, attractive foliage of Andover Green color, with a silvery sheen of Artemisia Green, good flower petalage ranging from 20 to 25 petals per flower, and a distinctive and attractive general color tonality of the flowers corresponding to Pale Cinnamon Pink, with the petals edged with Carmine and the lower half of the petals being overcast with Bordeaux.

No references cited.

ROBERT E. BAGWILL, *Primary Examiner.*